United States Patent
Amin

(10) Patent No.: US 6,932,836 B2
(45) Date of Patent: Aug. 23, 2005

(54) CATHETER AND STENT DELIVERY SYSTEM

(76) Inventor: Jatin Amin, 226 Santure Rd., Monroe, MI (US) 48162

( * ) Notice: Subject to any disclaimer, the term of this patent is extended or adjusted under 35 U.S.C. 154(b) by 339 days.

(21) Appl. No.: 10/202,437

(22) Filed: Jul. 24, 2002

(65) Prior Publication Data

US 2004/0034404 A1 Feb. 19, 2004

(51) Int. Cl.$^7$ ................................................. A61F 2/06
(52) U.S. Cl. .................. 623/1.11; 606/192; 606/194
(58) Field of Search ............................. 623/1.11, 1.1; 604/103.1, 103–103.04, 103.05, 103.09; 606/108, 191, 192, 194, 195; 600/585

(56) References Cited

U.S. PATENT DOCUMENTS

| | | |
|---|---|---|
| 4,644,936 A | 2/1987 | Schiff |
| 4,748,982 A | 6/1988 | Horzewski et al. |
| 4,881,547 A * | 11/1989 | Danforth .................... 606/194 |
| 4,921,479 A | 5/1990 | Grayzel |
| 4,988,356 A | 1/1991 | Crittenden et al. |
| 5,141,498 A * | 8/1992 | Christian ............... 604/167.03 |
| 5,171,222 A | 12/1992 | Euteneuer et al. |
| 5,409,458 A * | 4/1995 | Khairkhahan et al. . 604/103.08 |
| 5,462,530 A | 10/1995 | Jang |
| 5,667,514 A | 9/1997 | Heller |
| 5,709,658 A | 1/1998 | Sirhan et al. |
| 6,007,517 A * | 12/1999 | Anderson ............... 604/103.04 |
| 6,071,285 A | 6/2000 | Lashinski et al. |
| RE36,857 E | 9/2000 | Euteneuer et al. |
| 6,196,995 B1 | 3/2001 | Fagan |
| 6,251,119 B1 | 6/2001 | Addis |

* cited by examiner

Primary Examiner—Tan-Uyen T. Ho
(74) Attorney, Agent, or Firm—Harness, Dickey & Pierce, PLC

(57) ABSTRACT

A catheter and stent delivery system for alleviating a blockage within a vessel of a patient, allowing for the precise placement of a non-sliding balloon catheter assembly in a single step. The catheter assembly comprises a guide wire, a balloon wrapped around the distal end of the guide wire, and an inflation lumen running the length of the-guide wire, temporarily attached to said guide wire in a non-sliding means, and embodying an adapter to accommodate an inflation syringe, the inflation lumen and the guide wire. A stent can be utilized around the inflation balloon to further alleviate the stenosis.

17 Claims, 6 Drawing Sheets

CATHETER AND STENT DELIVERY SYSTEM

FIELD OF THE INVENTION

The present invention relates to the field of angioplasty. In particular, the present invention relates to a balloon catheter and guide wire that can be inserted into a patient in a single step, and furthermore, allow the exchange of the balloon catheter without removing the guide wire.

BACKGROUND OF THE INVENTION

The present invention relates to a catheter for use in angioplasty procedures. Over the last two decades, the medical procedure known as angioplasty has become widely accepted as a safe and effective method for treating various types of vascular stenoses. For example, angioplasty is widely used for opening stenosis throughout the vascular system and particularly for opening stenosis in coronary artery disease. At present, the most common form of angioplasty is called percutaneous transluminal angioplasty. This procedure utilizes an elongated, more or less, flexible dilation catheter with an inflatable balloon at its distal end. Using a fluoroscope and radio opaque dye for visualization a physician may steer the distal end of the balloon catheter into position through a guide catheter and across the stenosis. Once so positioned, the dilation balloon is inflated for a brief duration to open the artery and establish adequate blood flow.

Typically, inflation of the balloon is accomplished by supplying a pressurized fluid through an inflation lumen in the catheter. The lumen is connected to an apparatus which includes a source of pressurized inflation fluid and is located outside the patient's body. Conversely, applying a negative pressure until the inflation lumen collapses the balloon to its minimal dimension allows for removal of the balloon catheter from within the target blood vessel. Such an application of negative pressure to the balloon catheter is also used to ensure that the balloon has its minimal dimension during the insertion of the balloon to the treatment site.

In the past, a number of balloon catheter designs have been developed which contribute to the safety and acceptability of the PTCA or similar medical procedures. The most common design is known as "over the wire balloon catheter". Conventional dual lumen devices typically utilize a relatively large lumen for the passage of the guide wire and a second parallel lumen is provided for inflation and deflation of the balloon. Typically, a steerable guide wire is positioned within the larger lumen and the entire assembly is maneuvered into an initial position within the previously positioned guide catheter of large enough size to pass the balloon catheter therethrough. From here the guide wire can be rotated axially, extended or retracted into position across the lesion. The balloon dilation catheter is subsequently advanced along the guide wire in a sliding manner to position its deflated balloon across the lesion. Inflation of the balloon then effects the dilation of the stenosis. After the deflation, the deflated balloon is withdrawn in a sliding manner back in the guide catheter.

Though successful at opening stenotic lesions, this dual lumen catheter is relatively bulky and somewhat stiff as well. The technology has progressed to a point where these catheters can be used in a majority of the procedures, but the larger lumen still restricts the use of a smaller size guide catheter. These over the wire balloon catheters are difficult to use and require additional assistance or an implanting physician to control the guide wire during the positioning of the assembly because the movement of the catheter and guide wire are independent of each other. This complex coordinated activity requires both experience and skill and may result in slower insertion procedures than desired. This becomes especially important when angioplasty or stent placement are performed using distal emboli protection.

An alternative over the wire catheter assembly utilizes a non-removable guide wire that allows for longitudinal and axial movement. However, this design has a significant drawback because the entire guide wire catheter assembly must be removed to accomplish the replacement or exchange of the balloon. In some cases of PTCA, it is necessary to replace the balloon with one of a different diameter or configuration following initial dilatation. Additionally, cases of acute reclosure have been noted where the lesion re-closes following dilatation and removal of the balloon catheter. This alternative over the wire system adds to the difficulty of the subsequent procedures by requiring that the placement of the catheter renegotiate the entire vascular pathway without the advantage of the retained guide wire position. That is, when the catheter is pulled out to allow the catheter exchange, the path to the treatment site is at least partially lost because the guide wire comes out with the catheter assembly.

Another version of conventional balloon catheter is known as "monorail variance" of the standard balloon on the wire system and has been developed so that only a distal part of the balloon catheter tracks over the guide wire. These monorail catheter systems utilize a conventional balloon inflation lumen and a relatively short guiding or through-lumen for the guide wire at the distal end of the catheter. Use of this catheter involves insertion of the guide wire across the stenosis first and then advancing the monorail catheter to the stenosis site in a sliding manner. After deflation, the monorail catheter is withdrawn in the guide catheter in a sliding manner.

The principle benefits of monorail variant balloon catheters is the reduction of frictional drag over the length of the guide wire, which is external of the catheter over much of the length of the catheter, and ease of the balloon exchange. The monorail catheter provides for the ability to re-cross an acutely closed vessel or to exchange the balloon without removing or extending the guide wire. However, a disadvantage of this design is increased difficulty in steering the guide wire because the guide wire is not supported by the balloon catheter itself. Additionally, monorail catheters are at least of dual lumen configuration at the distal end. This design produces a larger profile for the catheter and a larger shaft size.

Another conventional balloon dilatation catheter design is the fixed wire or integrated "balloon on a wire dilatation catheter". This single lumen design utilizes a guide wire having a relatively small diameter positioned within an inflation lumen and is permanently fixed to the distal end of the dilation catheter. This design produces a low profile assembly which is able to cross severely narrow lesions and to navigate tortuous vascular pathways. Additionally, the fixed guide wire is bonded to the distal end of the balloon and improves the steerability and pushability of these designs. This aspect of the fixed wire catheter also enhances their maneuverability.

The thin shaft design of the guide wire of this catheter also improves visualization and enables all but the tightest critical lesions to be crossed. However, although able to provide relatively quick and simple balloon placement as well as providing access to the lesions otherwise unsuitable for PTCA, balloon on a wire systems sacrifice both ability to maintain the guide wire position across the lesion when exchanging balloons and also the safety advantage of being able to re-cross an acutely closed vessel without repositioning the entire assembly.

In view of the deficiencies of the conventional technology, it is an object of the present invention to provide a "balloon on a wire" dilatation catheter which incorporates all the benefits of the smallest diameter "fixed wire" system and in addition, it allows for the complete removal of the balloon while maintaining the wire position. When used as a stent delivery system for primary stenting, this device will provide an extremely low profile throughout its entire length and will be extremely flexible. A distal protection device can be easily added to this system as well, which will make the entire process an easy, single step.

SUMMARY OF THE INVENTION

In light of the aforementioned prior art designs, it is an object of the present invention to provide a catheter and stent delivery system with extremely low profile throughout the entire length of the catheter for the treatment of a stenosis within the arteries of a patient.

It is a further object of the present invention to provide a catheter and stent delivery system with a low profile throughout the entire length of the catheter having improved flexibility especially in the balloon segment.

Another object of the present invention is to provide a balloon and inflation lumen which are wrapped securely around the guide wire during insertion into the patient through temporary mechanical or chemical bonds, preventing any sliding movement between the guide wire and the balloon and inflation lumen. Upon inflation, the bonds disrupt releasing the guide wire from the inflation lumen and balloon.

Another object of the present invention is to provide a catheter wherein the inflation lumen and balloon are wrapped around the guide wire during insertion into the patient allowing for easy removal of the balloon and the inflation lumen from the patient after deflation, retaining the guide wire in position within the patient.

It is a further object of the present invention to provide for a catheter that comprises a guide wire and multiple inflation lumens and balloons of varying size that are inserted into the patient simultaneously allowing for a two-step angioplasty procedure without disturbing the guide wire position between steps.

Another object of the present invention is to provide a catheter that embodies optional expandable, cone-shaped gold markers attached to both the distal and proximal ends of the catheter balloon for ease of insertion of the catheter, and for monitoring the position of the balloon during insertion into the patient through fluoroscopy.

It is another object of the present invention to provide for a catheter and stent delivery system in which a stent is inserted within the stenosis of a patient, and subsequently allowing the removal of the balloon catheter and inflation lumen while maintaining the position of the guide wire within the patient.

It is a further object of the present invention to provide a balloon catheter and stent delivery system wherein the guide wire, inflation lumen and balloon are inserted into the patient simultaneously and positioned across the stenosis in one step without sliding movement between the guide wire and inflation lumen or balloon.

It is a final object of the present invention to provide a balloon catheter and stent delivery system which may be manufactured at a low cost and reduces the time required to accomplish the task of primary stenting.

The foregoing objects and others are accomplished in the preferred embodiment of the invention by a catheter and stent delivery system for use in an angioplasty procedure on a patient comprising three elements. The first element is a guide wire of which many different sizes and forms are available. The present invention is intended to cover many currently available guide wires as well as the ones that will be available in the future. The second element is an inflatable balloon having a proximal end and a distal end. The distal end is closed, preventing communication of the interior volume with the exterior environment. The proximal end of the inflatable balloon is connected to an inflation lumen. The elongated inflation lumen has a proximal end and a distal end. The distal end of the inflation lumen is connected to the proximal end of the balloon and the proximal end of the inflation lumen is connected to a special adapter that can be connected to an inflation device such as a syringe. The Inflation lumen and the balloon are at least partially wrapped around the guide wire in a manner which prohibits any sliding movement of the guide wire. The balloon is at least partially wrapped around the guide wire near the distal end of the guide wire and may further embody a stent wrapped around the balloon. This system of having the guide wire wrapped with the inflation lumen and the balloon provides for an extremely low profile for the entire length of the catheter system. The inflation lumen and balloon may be held in place temporarily by either mechanical means or some adhesive as needed. These temporary bonds subsequently disrupt for separation of the balloon and inflation lumen from the guide wire for removal there from. The balloon may be secured around the guide wire at a predetermined location from the distal tip of the guide wire so as to allow a balloon catheter system with short, medium or long protruding wire tips, depending on the user's preference. The guide wire can be of varying stiffness and various transition segments so as to provide smooth torqueing and advancement of the entire system into the appropriate position.

The third element of the system is a detachable clip device designed to specifically accommodate the inflation lumen and guide wire which become physically separate towards the proximal end of the system. This clip device holds the inflation lumen and guide wire together outside of the guiding catheter during maneuvering and advancement of the system into the appropriate position. Once the inflation of the balloon is carried out, the clip can be removed so that the wire can be left in place and the inflation lumen which is permanently connected to the clip, can be removed completely along with the balloon once the inflation is completed.

Two semicircular cone-shaped gold markers, may be implemented in the system as a means for providing a visual indicator for monitoring outside the patient and which are permanently attached to the distal and proximal ends of the balloons, allowing for easier insertion and maneuverability of the catheter device during insertion and removal, and further allow enhanced positioning of the balloon and stent by monitoring through fluoroscopy outside the patient.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
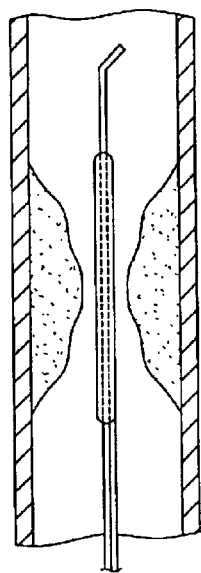
FIG. 1 is a cross-sectional view of the pre-inflated balloon catheter in position across a partial stenosis.
Figure 2:
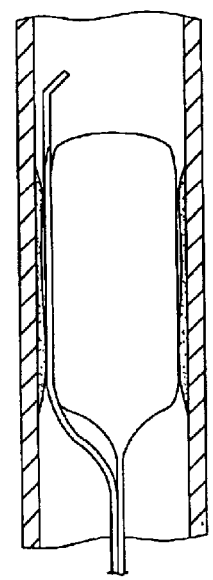
FIG. 2 is a cross-sectional view of the inflated balloon catheter alleviating the stenosis.

Referring now to FIGS. 1 through 4, the balloon catheter with or without a stent delivery system of the present invention is shown positioned within an arterial vessel such as a coronary vessel over a partial stenosis. Referring now specifically to FIG. 1, the balloon catheter 10 is shown within an arterial vessel 12 having a stenosis 14 comprising a guide wire 20, an inflation lumen 30 and a balloon 40 attached to the inflation lumen 30 and wrapped around the guide wire 20, prior to inflation from an external source. FIG. 2 depicts the balloon catheter 10 in its inflated state, wherein the balloon 40 is inflated by way of the inflation lumen 30 from an external source. Once inflated, the balloon 40 becomes unwrapped from the guide wire 20 and exerts a force against the arterial walls and compresses the stenosis, alleviating the blockage. In the event that a stent was pre-mounted to the balloon 40, it would be deployed upon inflation of the balloon 40.

Figure 3:
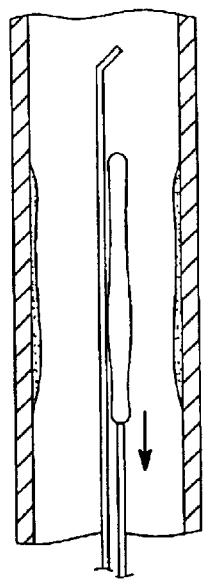
FIG. 3 is a cross-sectional view of the deflated balloon catheter after treating the stenosis, prior to withdrawal of the balloon and inflation lumen.
Figure 4:
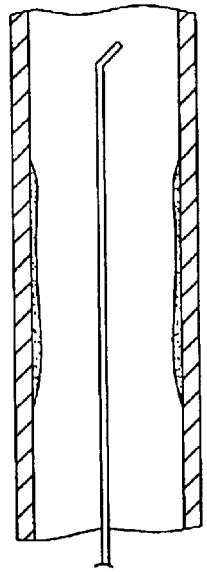
FIG. 4 is a cross sectional view of the remaining guide wire of the balloon catheter, after the balloon and inflation lumen are removed.

FIG. 3 shows the balloon catheter 10 subsequent to the deflation of balloon 40 following the alleviation of the stenosis 14 in an arterial vessel 12. Once deflated, the balloon 40 and inflation lumen 30 are no longer wrapped around the guide wire 20 and are positioned adjacent to the guide wire 20. This allows the subsequent removal of the inflation lumen 30 and balloon 40 while maintaining the guide wire 20 in position within the arterial vessel 12 as depicted in FIG. 4. By maintaining the guide wire 20 within the arterial vessel 12, it allows an optional secondary balloon and inflation lumen to be inserted along the guide wire 20 for further alleviation of the stenosis.

Figure 5:
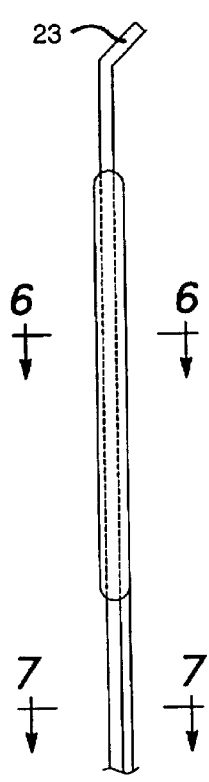
FIG. 5 is a partial side view of the balloon catheter showing the balloon and the inflation lumen wrapped around the guide wire.
Figure 8:
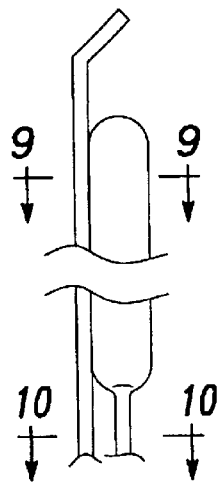
FIG. 8 is a partial side view of the balloon catheter wherein the inflated balloon is disposed along side of the guide wire.

Referring now to FIGS. 5 and 8, the catheter 10 is shown having a guide wire 20 with a balloon 40 and an inflation lumen 30. FIG. 5 specifically depicts balloon 40 as being tightly wrapped around guide wire 20, exemplifying the pre-inflated state. The guide wire 20 has a bent, distal end 23 to allow the steering of the catheter 10 in tortuous locations or in a side branch of a vessel by the user. FIG. 8, shows the distal end of the balloon catheter 10 wherein the balloon 40 is inflated, causing it to become unwrapped from the guide wire 20 and repositioned adjacent to the guide wire 20. Furthermore, when the balloon 40 becomes unwrapped, the corresponding inflation lumen 30 separates from the guide wire 20 and also becomes repositioned adjacent to the guide wire 20. Upon deflation, the inflation lumen 30 and balloon 40 are allowed to be withdrawn from the arterial vessel 12 while maintaining the guide wire 20 within, providing for the insertion of a second balloon 40 and inflation lumen 30 along the guide wire 20.

Figure 6:
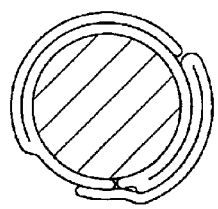
FIG. 6 is a cross sectional view of FIG. 5 taken along line 6 showing the balloon wrapped around the outside of the guide wire in its pre-inflated stage.
Figure 9:
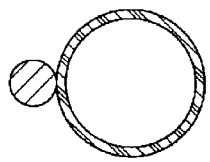
FIG. 9 is a cross-sectional view of FIG. 8, taken along line 9 showing the inflated balloon adjacent to the guide wire.
Figure 7:
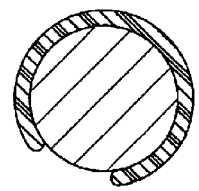
FIG. 7 is a cross-sectional view of FIG. 5, taken along line 7 showing the inflation lumen partially encircling the guide wire.
Figure 10:
FIG. 10 is a cross-sectional view of FIG. 8, taken along line 10, showing the inflation lumen adjacent to the guide wire.

Referring now to FIGS. 6, 7, 9, and 10, cross sectional views of the balloon catheter 10 are shown at various locations and states depicting the guide wire 20, the inflation lumen 30 and balloon 40. Specifically, FIG. 6 shows a cross-sectional view of FIG. 5 taken along line 6 showing the guide wire 20, and the pre-inflated balloon 40 wrapped around the guide wire 20. FIG. 7 illustrates a cross sectional view of FIG. 5 taken along line 7 showing the guide wire 20 and the pre-inflated inflation lumen 30 partially wrapped around the guide wire 20. FIG. 9 shows a cross sectional view of FIG. 8 taken along line 9 showing the guide wire 20 and the inflated balloon 40 unwrapped and oriented adjacent to the guide wire 20, while FIG. 10 depicts a cross sectional view of FIG. 8 taken along line 10 showing the guide wire 20 and the inflated and separated inflation lumen 30.

Figure 11:
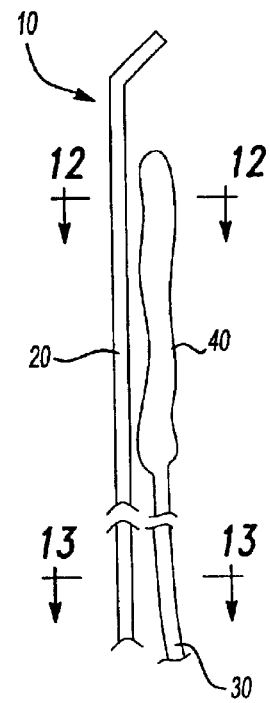
FIG. 11 is a partial side view of the deflated balloon catheter after treating a stenosis, prior to removal.
Figure 12:
FIG. 12 is a cross-sectional view of FIG. 11, taken along line 12, showing the deflated balloon adjacent to the guide wire after treating the stenosis.
Figure 13:
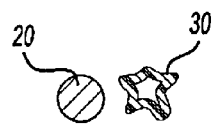
FIG. 13 is a cross-sectional view of FIG. 11, taken along line 13 showing the deflated inflation lumen adjacent to the guide wire.

FIG. 11 shows the distal end of the balloon catheter 10 of the present invention in the post deflation state. Once the stenosis has been alleviated, balloon 40 is deflated, leaving the inflation lumen 30 and balloon 40 deflated adjacent to the guide wire 20. FIG. 12 is a cross-sectional view of FIG. 11 taken along line 12 depicting the deflated balloon 40 along side the guide wire 20, while FIG. 13 is a cross sectional view of FIG. 11 taken along the line 13 showing the deflated inflation lumen 30 and the guide wire 20.

Figure 14:
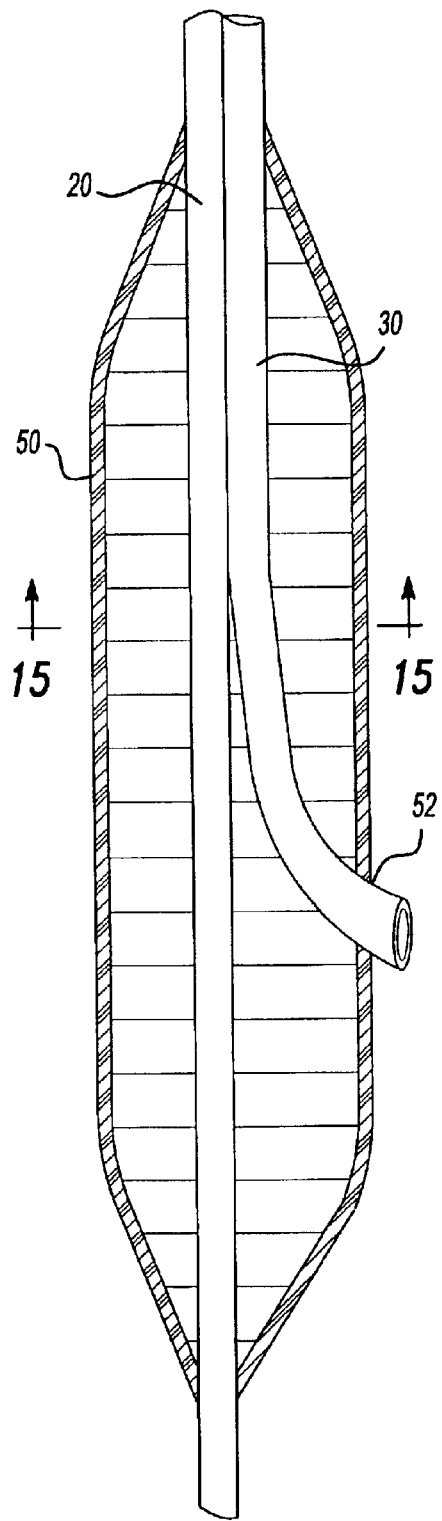
FIG. 14 is a sectional side view of the torquer for manipulating the inflation lumen and the guide wire of the balloon catheter outside the patient.
Figure 15:
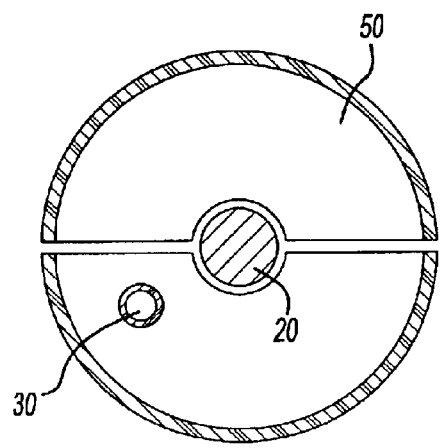
FIG. 15 is a cross sectional view of the torquer, guide wire and inflation lumen.

FIGS. 14 and 15 show a torquer 50 that holds the guide wire 20 in place, allowing the manipulation of the catheter in an axial and rotational manner within the arterial vessels. It provides for an aperture 52 for attachment to an inflation syringe. The aperture 52 is in direct communication with the inflation lumen 30. After balloon 40 is deflated, torquer 50 may be opened up, releasing the guide wire 20, providing for the removal of balloon 40 and inflation lumen 30.

Figure 16:
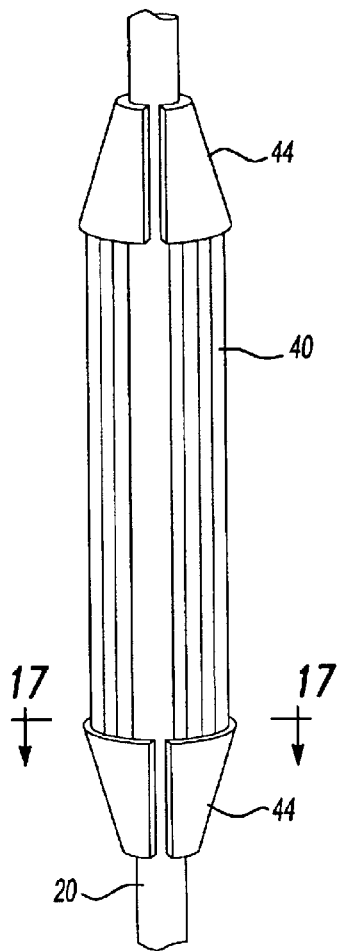
FIG. 16 is a side view of the balloon wrapped around the guide wire, prior to inflation, with gold markers attached to the proximal and distal ends of the balloon.

Referring now to FIG. 16, a close-up view of the uninflated balloon 40 wrapped around the guide wire 20 of the present invention is illustrated. In this preferred embodiment, a pair of optional gold markers 44 are attached to both the distal and proximal ends of the uninflated balloon 40. Each gold marker is comprised of two pieces having a generally frustoconical shape. The markers 44 are attached to both ends of the wrapped balloon 40 in opposing orientations to provide for easy maneuverability of the balloon catheter 10 through the arterial vessels 12 of the patient. The markers 44 further provide for a means of tracking the movement of the balloon catheter 10 through the arterial vessels 12 while inserting, removing, and positioning the balloon catheter 10 within the patient by means of monitoring through fluoroscopy.

Figure 17:
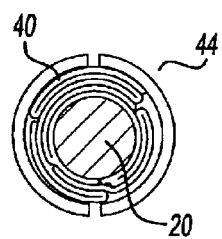
FIG. 17 is a cross-sectional view of FIG. 16, taken along line 16 showing the guide wire, the balloon wrapped around the guide wire, and the gold markers.

These markers 44 are further depicted in the cross-sectional view of FIG. 17 which is taken from line 17 of FIG. 16. Illustrated is the balloon 40 prior to inflation wrapped around the guide wire 20 with the two-piece gold marker 44 attached to the balloon. When the balloon catheter 10 is positioned correctly in the arterial vessel 12 across a stenosis, the balloon 40 is inflated by way of the inflation lumen 30, and as it expands and separates away from the guide wire 20, the two halves that make up each gold marker 44 separate apart but maintain their attachment to the distal and proximal ends of balloon 40. When balloon 40 is subsequently deflated after alleviation of the stenosis 14, the gold markers 44 maintain their attachment to balloon 40 for withdrawal therewith along with the inflation lumen 30 while maintaining the guide wire 20 within the vessel 12.

Figure 18:
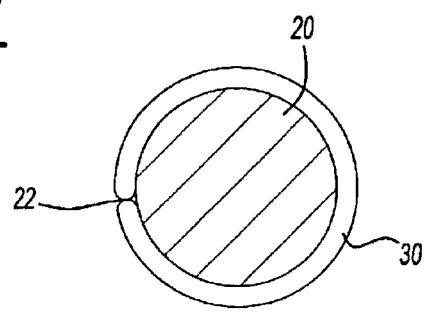
FIG. 18 is a cross-sectional view of one embodiment of the inflation lumen fully encircling the guide wire.
Figure 19:
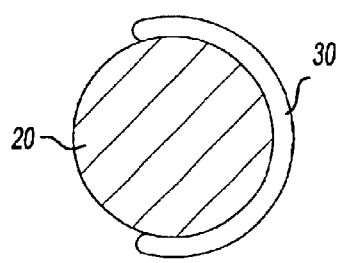
FIG. 19 is a cross-sectional view of an alternate embodiment of the inflation lumen partially encircling the guide wire.
Figure 20:
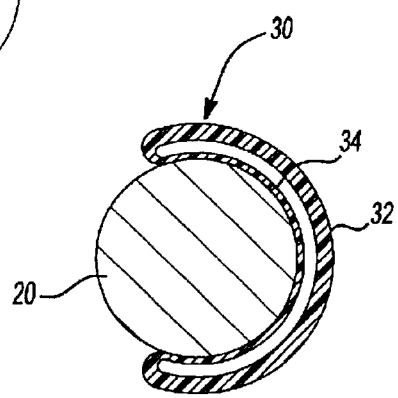
FIG. 20 is a cross-sectional view of an alternative embodiment of the inflation lumen having a semi-rigid outer-shell with some elasticity and an inner-shell of pliable thin material, allowing the inflation lumen to wrap tightly around the guide wire.

FIGS. 18 through 20 illustrate cross-sectional views of alternative embodiments to the inflation lumen 30, as shown wrapped around the guide wire 20 in the pre-inflated stage. Specifically, FIG. 18 shows the preferred embodiment wherein the inflation lumen 30 wraps completely around the guide wire 20. During inflation, inflation lumen 30 separates from the guide wire 20 for subsequent removal from the arterial vessel, leaving the guide wire 20 in position. FIG. 19 depicts a cross sectional view of the inflation lumen 30 in the pre-inflated state, similar to that of FIG. 18, but the inflation lumen 30 only wraps partially around the guide wire 20. During inflation, this embodiment may provide for easier separation of the inflation lumen 30 from the guide wire 20. Finally, FIG. 20 is a cross-sectional view of a third embodiment of the inflation lumen 30, comprising a semi-rigid outer shell 32, that provides for a predetermined amount of elasticity and an inner surface 34 of a pliable thin material. This may allow the guide wire 20 to be contained within the folded inflation lumen 30 easily while still providing for a simple means of separation when inflation is so desired. In addition, this will provide for additional stiffness resulting in greater pushability.

Figure 21:
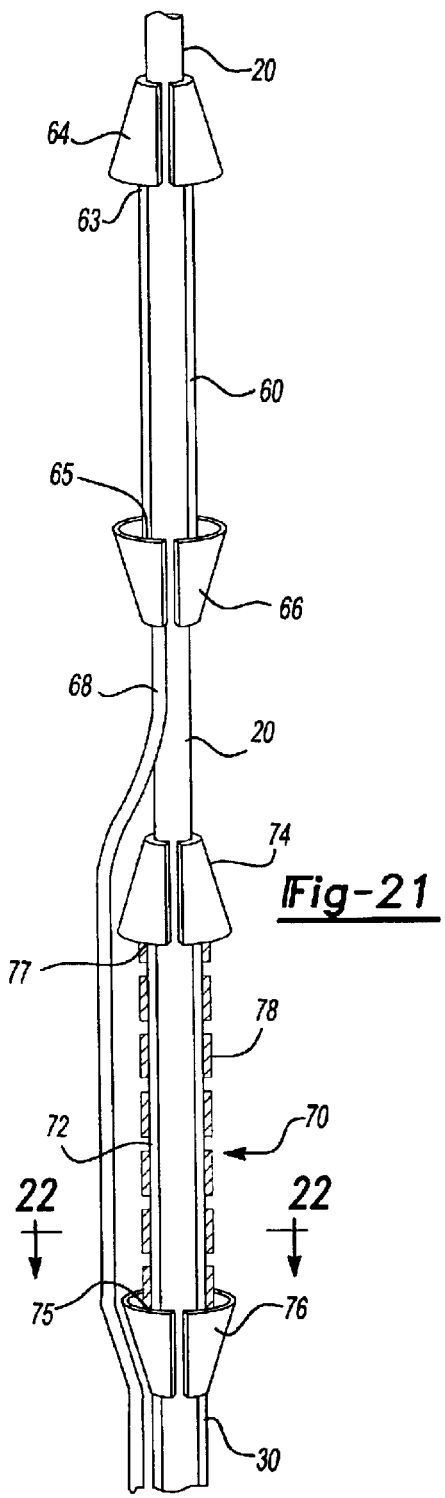
FIG. 21 is a side view of a balloon catheter embodying two separate balloons with gold markers on a single guide wire, the latter of which embodies a stent wrapped around the balloon.

Referring now to FIG. 21, the distal end of the balloon catheter 10 of the present invention is shown having a first balloon element 60 and a second balloon element 70. Both the first balloon element 60 and the second balloon element 70 are located inline on the guide wire 20. The first balloon element 60 comprises a first balloon 62 of a predetermined size, wrapped around the guide wire 20. Attached to the balloon 62 are a first set of gold markers 64 and a second set of gold markers 66 attached to the distal end 63 and the proximal end 65 of the first balloon 62. The first balloon 62 has a corresponding inflation lumen 68 which wraps around guide wire 20 and travels proximally down guide wire 20 towards the proximal end of balloon catheter 10.

A predetermined distance proximal the first balloon element 60 on the guide wire 20, is a second balloon element 70. Similar to the first balloon element 60, the second balloon element 70 comprises a balloon 72 wrapped around guide wire 20 and having a corresponding first and second set of gold markers 74 and 76 respectively, attached to the proximal end 75, and distal end 77 of the balloon 72, respectively. The second balloon 72 will have a generally larger inflated diameter than the first balloon 62, providing for further alleviation of the stenosis 14. A stent 78 may be embodied around the pre-inflated second balloon 72 which will expand as the balloon 72 is inflated. As the balloon 72 is deflated, the stent 78 will maintain its expanded state, pressing against the alleviated stenosis, while the deflated balloon 72 and corresponding secondary inflation lumen 73 may be withdrawn from the arterial vessel 12 while maintaining the guide wire 20 in position within the arterial vessel 12. The inflation lumen 68 of the first balloon element 60 travels along the outside of the second balloon element 70 adjacent to the gold markers 74 and 76, the stent 78, and the balloon 72. The second inflation lumen 73 corresponding to balloon 72 also runs proximally down guide wire 20.

When inserting this dual type of balloon catheter, the treating physician guides the balloon catheter 10 through the arterial vessels 12 to the location of the stenosis 14, wherein when he positions the first balloon element 60 over the stenosis 14 and proceeds to inflate the first inflation lumen 68 and subsequently, the first balloon 62 as well. Once the stenosis 14 has been treated, the physician deflates the first balloon element 60 and removes balloon 62 and corresponding inflation lumen 68. The physician then proceeds to guide the balloon catheter 10 further into the arterial vessels until the second balloon element 70 is positioned over the same stenosis 14. The second balloon 72, generally of a larger diameter, can allow further alleviation of the stenosis 14 by expanding further radially and henceforth, exerting greater pressure against the stenosis 14. This second balloon element 70 may embody a stent 78 which may be inserted within the stenosis 14 to further enhance the alleviation. After deflation, the second inflation lumen 73 and attached second balloon 72 with attached gold markers 74 and 76 may be withdrawn from the patient's arterial vessel 12, maintaining guide wire 20 in position for future catheter utilization or subsequent removal.

Figure 22:
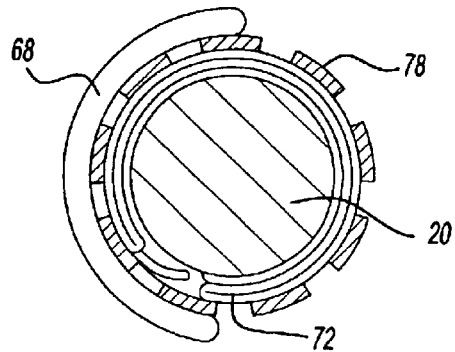
FIG. 22 is a cross-sectional view of FIG. 21, taken along line 22 showing the guide wire, the un-inflated balloon, a stent, and the inflation lumen of a second balloon.
Figure 23:
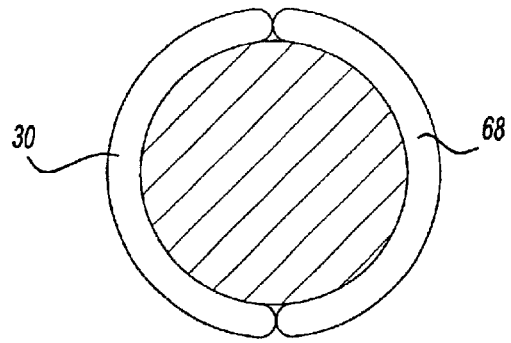
FIG. 23 is a cross sectional view of the guide wire having a first and second inflation lumen partially wrapped around it for the inflation of a distal and a proximal balloon respectively.

FIG. 22 illustrates a cross-sectional view of FIG. 21, taken at line 22 showing the second balloon element 70. The first inflation lumen 68 for inflating the first balloon element 60 is partially wrapped around the outside stent 78 of the second balloon element 70. The second balloon 72 in its pre-inflated stage is depicted wrapped around the guide wire 20 underneath the stent. FIG. 23 shows a cross sectional view of FIG. 21, along line 23, depicting the guide wire 20 with both inflation lumens 68 and 30 respectively wrapped around the guide wire 20, corresponding to their respective distal and proximal balloons.

Figure 24:
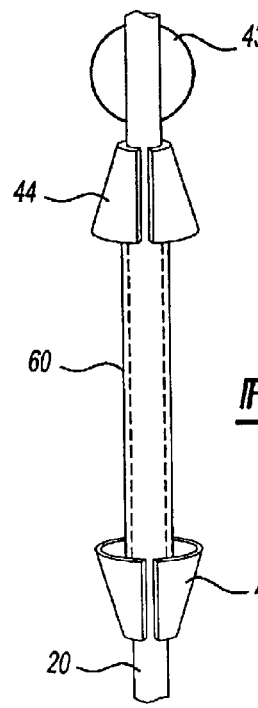
FIG. 24 is a side view of a balloon catheter embodying a distal protection balloon on the guide wire.

FIG. 24, shows a partial side view of the balloon catheter 10 at the location of the balloon 40, in its pre-inflated position wrapped around the guide wire 20, embodying a pair of gold markers 44 attached to the distal and proximal ends of the balloon 40. A distal protection balloon 43 is shown attached to the guide wire 20, distal to the balloon 40 and proximal to the distal end of the guide wire. The protection balloon 43 prevents the distal embolization atherosclerotic or thrombotic material. Different types of distal protection devices may be incorporated in place of the balloon.

Figure 25:
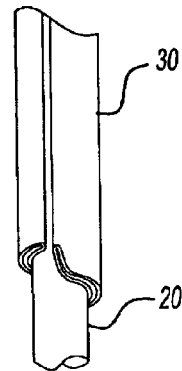
FIG. 25 is a fragmentary side view of the guide wire and the encircling inflation lumen.
Figure 26:
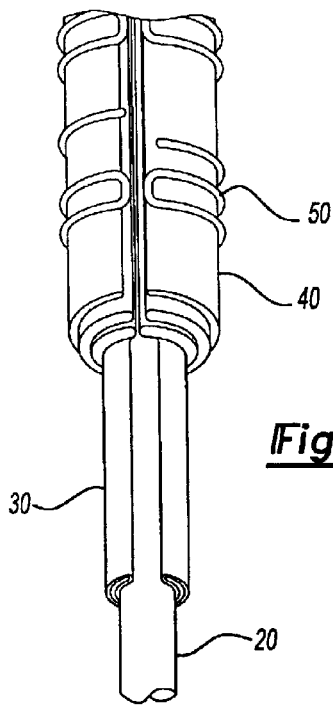
FIG. 26 is a fragmentary side view of the balloon catheter at the location of the balloon having a stent in place around the pre-inflated balloon.
Figure 27:
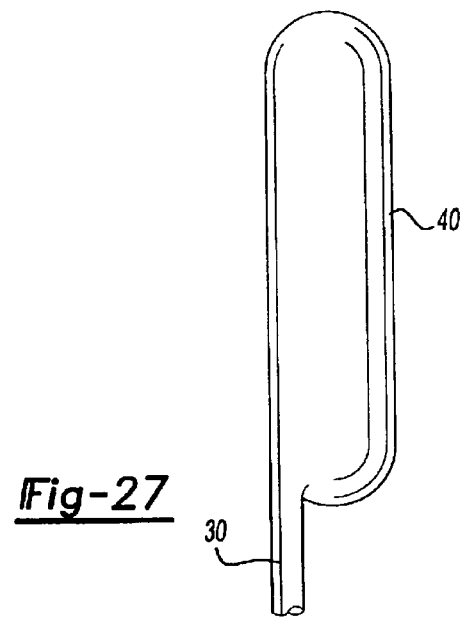
FIG. 27 is a plan side view of an alternative embodiment to the balloon having an offset attachment of the inflation lumen.

FIGS. 25 and 26 show a broken side view of the balloon catheter 10 of the present invention. FIG. 25 shows a partial cutaway view of the inflation lumen 30 wrapped around the guide wire which makes up the majority of the length of the balloon catheter 10. FIG. 26 depicts a partial cutaway of the balloon catheter 10 at the location of the balloon 40 wherein the balloon 40 is wrapped around the guide wire 20 in its pre-inflated position and embodies a stent 50 around the balloon 40. The inflation lumen 30 is partially wrapped around the guide wire 20, also illustrating the pre-inflated position. Upon inflation by an external force, the inflation lumen 30 and the balloon 40 will expand radially, unwrapping from the guide wire 20 and forcing the stent 50 outward radially, alleviating the stenosis 14 within the arterial vessel 12 of the patient. Once the balloon 40 and attached inflation lumen 30 are allowed to deflate, the stent 50 remains in its radially expanded position with the arterial vessel and the inflation lumen 30 and balloon 40, which are now unassociated with the guide wire 20, and may be withdrawn from the patient while maintaining the guide wire 20 in position.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A catheter and stent delivery system, for alleviating a stenosis of a vessel comprising:

a guide wire;

at least one balloon, having distal and proximal ends;

at least one inflation lumen having proximal and distal ends;

connection means releasably securing said balloon and said inflation lumen against relatively longitudinal and rotational movement relative to said guide wire, and being operable upon inflation of said balloon to permit relative longitudinal movement between said balloon and lumen relative to said guide wire;

wherein said balloon, inflation lumen and guide wire are temporarily bonded together as a single unit and inserted into a patient in a non sliding manner.

2. The catheter in claim 1 wherein said guide wire has a distal end extending into the vessel of the patient, and a proximal end extending outside the patient for manipulation of said catheter.

3. The catheter of claim 1 wherein said distal end of said balloon is closed, and said proximal end of said balloon connects with the said distal end of said inflation lumen, wherein the balloon may be inflated to desired diameter.

4. The catheter of claim 3 wherein said balloon is wrapped at least partially around said guide wire prior to inflation, a predetermined distance from the distal end of said guide wire as users preference.

5. The catheter of claim 3 wherein said balloon unwraps from guide wire upon inflation.

6. The catheter of claim 1 wherein said inflation lumen is formed of a flexible material comprising a tube wrapped at least partially around said guide wire.

7. The catheter of claim 6 wherein said distal end of said inflation lumen attaches to said proximal end of said balloon, and said proximal end extending outside the patient is connected to an adapter, wherein said adapter may be connected to an inflation syringe for inflation of said balloon.

8. The catheter of claim 6 wherein said inflation lumen has a flexible inner wall adjacent the guide wire and a semi-rigid outer wall of a predetermined degree of elasticity, maintaining the inflation lumen wrapped around the guide wire.

9. The catheter of claim 8 wherein said inflation lumen separates from said guide wire upon inflation.

10. The catheter of claim 1 wherein said balloon has an expandable stent around the exterior of said balloon.

11. A catheter and stent delivery system, for alleviating a stenosis of a vessel during an angioplasty procedure comprising:

a guide wire;

at least one balloon having distal and proximal ends;

at least one inflation lumen having proximal and distal ends, said inflation lumen is attached to said guide wire by temporary means, preventing longitudinal and rotational movement relative to said guidewire, and to be released upon inflation of said inflation lumen and said balloon, for a subsequent removal of said inflation lumen and said balloon;

a means for providing a visual indicator during said angioplasty procedure;

wherein said balloon, inflation lumen and guide wire are temporarily bonded together as a single unit and inserted into a patient in a non sliding, non rotational manner.

12. The catheter of claim 11 wherein said means for providing the visual indicator is one or more gold markers comprised of two pieces, attached to said proximal and distal ends of the balloon, for simultaneous insertion with said guidewire, wherein said gold markers split, and expand with the inflation of said balloon.

13. The catheter of claim 12 wherein said gold markers remain attached to said balloon after deflation, and are removed when the balloon and said inflation lumen are withdrawn.

14. The catheter of claim 11 wherein said balloon and attached inflation lumen may be withdrawn from patient independently from said guide wire, following inflation and subsequent deflation of said balloon.

15. A method for the treatment of vascular stenosis comprising:
   inserting as a single unit, a balloon catheter assembly comprising a guide wire, balloon, and inflation lumen, into a vessel across a stenosis in a single step without any sliding or rotational movement between the guide wire and the inflation lumen or balloon;
   wherein said inflation lumen and said balloon are attached to said guide wire by a temporary means, preventing longitudinal and rotational movement relative to said guidewire, and to be released upon inflation of said inflation lumen and said balloon, for the subsequent removal of said inflation lumen and said balloon;
   inflating said balloon to desired diameter so as to treat said stenosis or deliver a stent that is pre-mounted to said balloon prior to insertion that is subsequently expanded by radial force of said balloon;
   deflating said inflation lumen and said balloon;
   separating said balloon and said inflation lumen from said guide wire; and
   removing said balloon and said inflation lumen from the patient, while maintaining said guide wire in place across said stenosis.

16. The method for the treatment of vascular stenosis of claim 15, wherein said balloon catheter assembly further comprises a deliverable stent.

17. A catheter and stent delivery system, for alleviating a stenosis of a vessel during an angioplasty procedure comprising:
   a guide wire;
   at least one balloon, having distal and proximal ends, said balloon temporarily secured to and wrapped around said guidewire by selectively releasable means, preventing longitudinal and rotational movement of said balloon relative to said guidewire;
   a least one inflation lumen attached to said balloon having proximal and distal ends, said inflation lumen temporarily secured to said guidewire by the selectively releasable means, preventing longitudinal and rotational movement of said lumen relative to said guidewire during insertion of said catheter and stent, delivery system; and
   a means for providing a visual indicator comprising one or more gold markers comprised of two pieces, attached to said proximal and distal ends of the balloon, for simultaneous insertion with said guidewire, said gold markers split and expand with the inflation of said balloon, but remain attached to said balloon, and are removed when the balloon and said inflation lumen are withdrawn;
   wherein said guide wire, said at least one balloon, said at least one inflation lumen, and said means for providing a visual indicator are temporarily bonded together as a single unit and inserted into a patient in a non-sliding manner.

* * * * *